United States Patent [19]
Harrah, Jr.

[11] Patent Number: 5,782,250
[45] Date of Patent: Jul. 21, 1998

[54] DENTAL FLOSSING TOOL

[76] Inventor: Larry C. Harrah, Jr., 503 W. 14th, Atlantic, Iowa 50022

[21] Appl. No.: 777,387

[22] Filed: Dec. 27, 1996

[51] Int. Cl.$^6$ .................................................. A61C 15/04
[52] U.S. Cl. .................................. 132/327; 132/323
[58] Field of Search ............................... 132/323, 324, 132/325, 326, 327

[56] References Cited

U.S. PATENT DOCUMENTS

| | | | |
|---|---|---|---|
| 2,163,500 | 6/1939 | Shepard | 132/326 |
| 2,197,345 | 4/1940 | Meyer | 132/325 |
| 2,277,865 | 3/1942 | Jurovaty | 132/326 |
| 3,311,116 | 3/1967 | Foster . | |
| 3,387,615 | 6/1968 | Mackew | 132/323 |
| 3,734,107 | 5/1973 | Thierman . | |
| 3,747,611 | 7/1973 | Bennington . | |
| 3,847,168 | 11/1974 | Schlegel . | |
| 3,910,294 | 10/1975 | Reed . | |
| 4,041,962 | 8/1977 | Johansson et al. . | |
| 4,655,233 | 4/1987 | Laughlin . | |
| 4,655,234 | 4/1987 | Bowden . | |
| 4,936,326 | 6/1990 | Eckroat | 132/323 |
| 4,966,176 | 10/1990 | Lachenberg . | |
| 5,183,065 | 2/1993 | Mason . | |
| 5,188,133 | 2/1993 | Romanus . | |
| 5,253,661 | 10/1993 | Alonzo . | |
| 5,261,430 | 11/1993 | Mochel . | |
| 5,392,795 | 2/1995 | Gathani . | |
| 5,423,338 | 6/1995 | Hodge et al. . | |
| 5,482,466 | 1/1996 | Haynes . | |
| 5,638,841 | 6/1997 | Levine | 132/323 |

FOREIGN PATENT DOCUMENTS

| | | | |
|---|---|---|---|
| 2237203 | 5/1991 | United Kingdom | 132/334 |
| 2272161 | 5/1994 | United Kingdom | 132/323 |

*Primary Examiner*—Ralph A. Lewis
*Attorney, Agent, or Firm*—Chase & Yakimo

[57] ABSTRACT

A flossing tool includes a handle, a neck and a head at the distal end of the neck. A spool of floss is placed in a compartment within the handle with the free end of the floss being extended from the compartment and over a series of ridges traversing the neck. The floss is wound about four lobes on the head so as to present first and second laterally spaced-apart stretches of floss. The free end of the floss is then wound about a pin on the neck so as to place initial tension on the wound floss. A locking device engages the ridges on the neck so as to clamp the dental floss to the neck and place additional tension on the wound floss. Accordingly, first and second opposed stretches of tensioned floss are available to clean the upper and lower teethlines. A cutter blade on the neck allows the user to sever the end of the floss upon use. The angles between the handles, neck and floss head are selected so as to assist the user in flossing.

19 Claims, 7 Drawing Sheets

DENTAL FLOSSING TOOL

BACKGROUND OF THE INVENTION

This invention relates to a dental flossing tool and, more particularly, to a device for placing first and second lines of the dental floss in proper tension for subsequent effective use.

Various dental floss tools have been proposed in the prior art references cited herein. Although assumably effective in operation, it is desirable to have a dental flossing tool which presents the floss at a sufficient tension so as to efficiently provide its proper cleaning function. Moreover, it is also desirable to have a tool which presents first and second stretches of the floss at an operative position for use on the upper and lower teethlines.

In response thereto I have provided a dental flossing tool presenting a handle with compartment for holding a spool of dental floss therein. The floss extends from the handle compartment and wraps around corner lobes of a floss head, the spaced-apart lobes presenting first and second spaced-apart longitudinal stretches of dental floss on opposed sides of the head. The free end of the dental floss is wrapped around a tension pin or pins which initially tensions the wound floss. A locking device, swingably mounted on a neck intermediate the handle and the floss head, places additional tension on the wound floss. A blade on the neck enables the user to sever a used portion of the dental floss subsequent to use.

Accordingly, it is a general object of this invention to provide a dental flossing tool which presents and maintains operative tensions on the dental floss to enhance use.

Another object of this invention is to provide a tool, as aforesaid, the flossing tool having a head which presents first and second laterally spaced-apart stretches of dental floss under tension for effective use.

A still further object of this invention is to provide a dental tool, as aforesaid, having tension pin(s) for winding the floss therearound so as to initially tension the wound dental floss.

A further object of this invention is to provide a flossing tool, as aforesaid, having a locking device thereon so as to provide additional tension on the wound floss line.

Another particular object of this invention is to provide a dental flossing tool, as aforesaid, having a blade thereon for severing a selected used portion of the free end of the wound floss.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENT

Turning more particularly to the drawings, the tool 100 comprises an elongated handle 200, neck 300 and floss head 400 extending therefrom.

Figure 4:
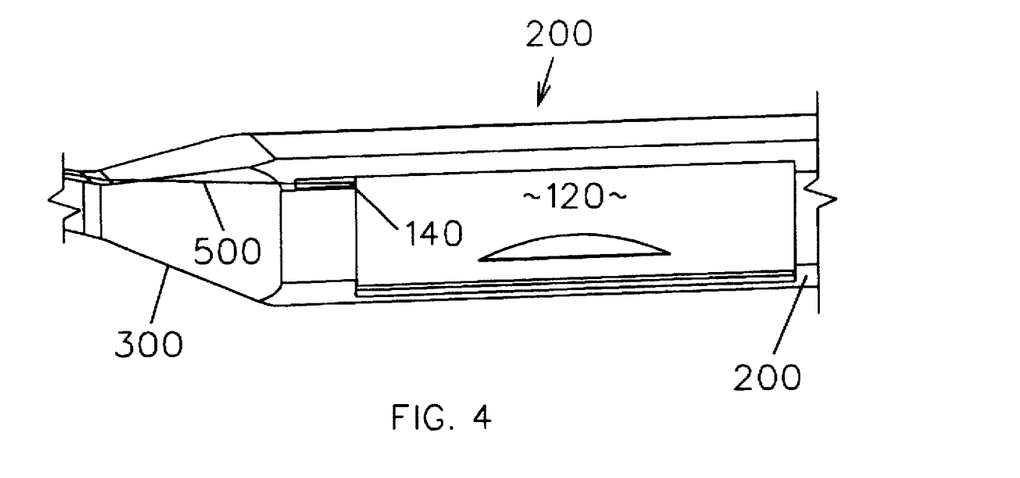
FIG. 4 is a fragmentary view of the handle of the flossing tool of FIG. 1 on an enlarged scale.
Figure 5:
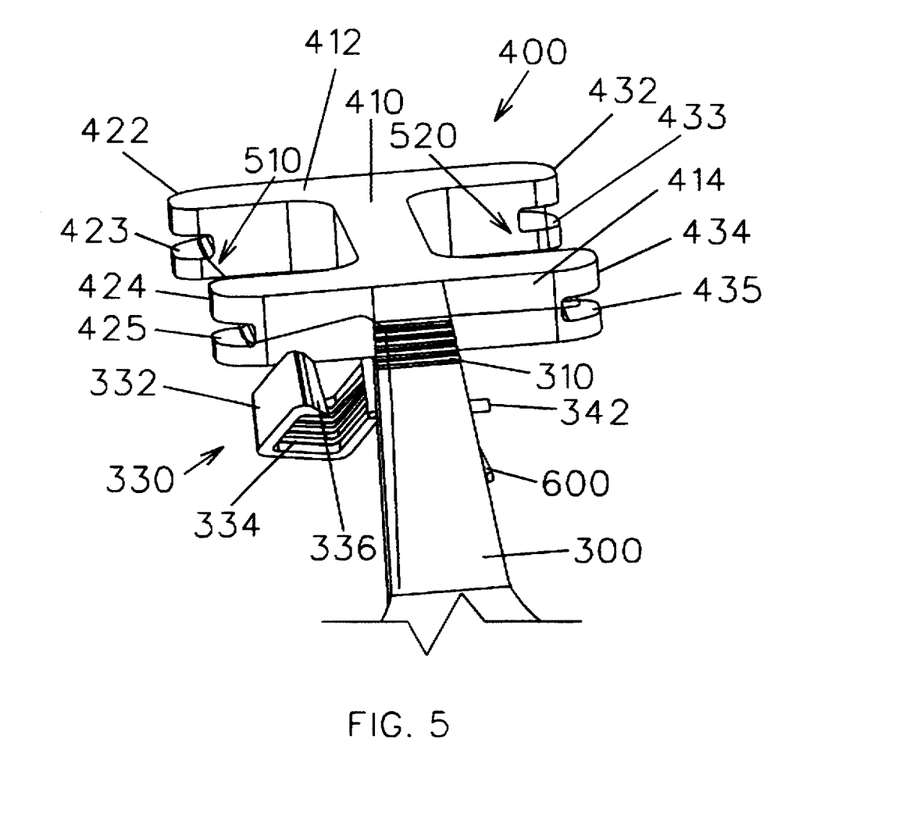
FIG. 5 is a rear fragmentary view of the floss head, the locking device in an unlocked position displaced from the neck.
Figure 6:
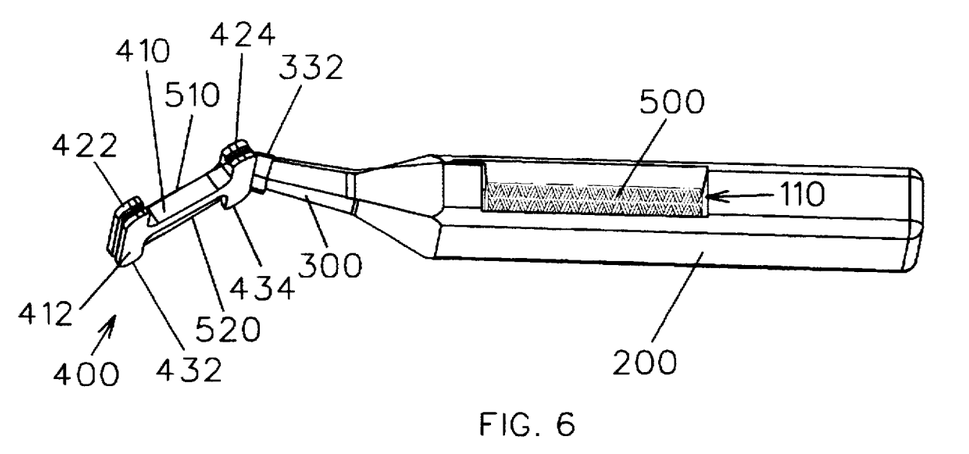
FIG. 6 is the FIG. 1 view of the tool with door removed to show the floss stored within the handle compartment.

Handle 200 is an elongated construction and includes therein a compartment 110 with access thereto provided by a pivotal door 120. A spool of dental floss 500 is secured within the compartment 110 with the free end of the floss 500 extending through a slot 140 adjacent the door 120 of the handle 200. The slot 140 longitudinally lies along the side of the handle 200 and presents a portion of the path for the floss extending from compartment 110.

Extending from the handle 200 at an upward angle between five and ten degrees is a tapered neck 300. A plurality of spaced-apart ridges/grooves 310 laterally extending across the neck 300. A lock assembly 330 is swingably mounted to one side of the neck 300 and includes a U-shaped clamp 332 having ridges/grooves 334 thereon which are designed to mesh with the ridges 310 extending across the neck 300.

Figure 7:
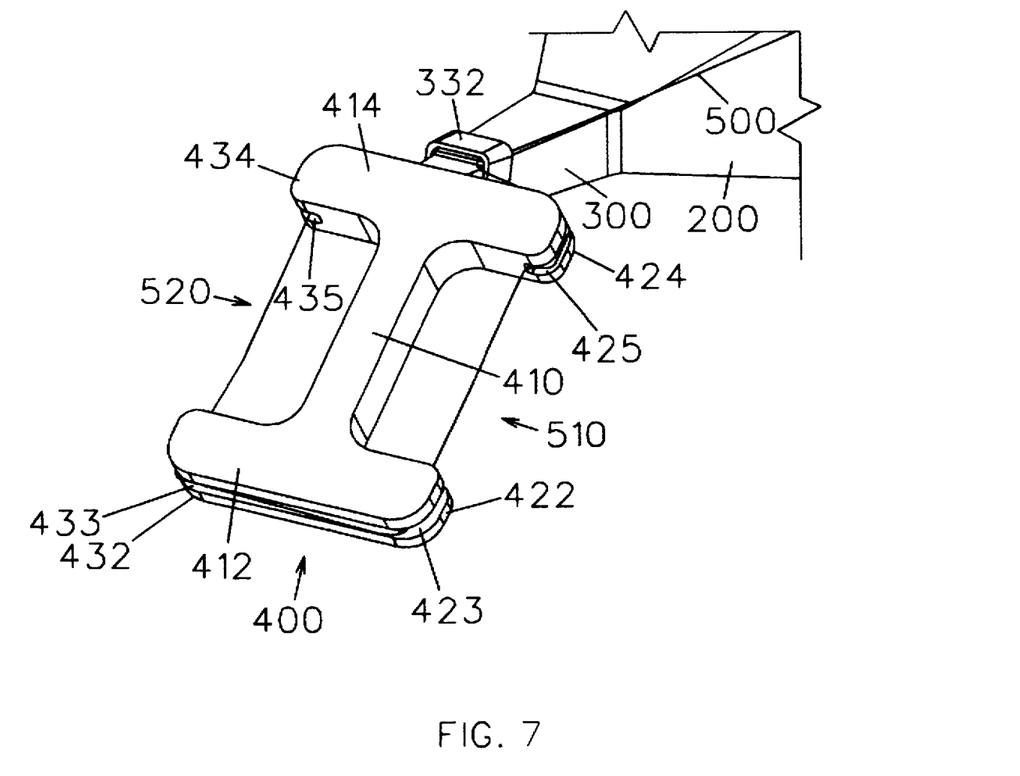
FIG. 7 is a front fragmentary, perspective view, on an enlarged scale, of the head of the dental flossing tool.

Attached to the distal end of neck 300 at a downward angle of approximately 45 degrees is a floss head 400 having a central longitudinal beam 410 and first 412 and second 414 traverse beams. Corner lobes 422, 432, 424, 434 extend from the ends of the respective cross beams 412, 414. Within each lobe is a groove 423, 433, 425, 435 for presenting channels for floss passing therethrough.

Figure 2:
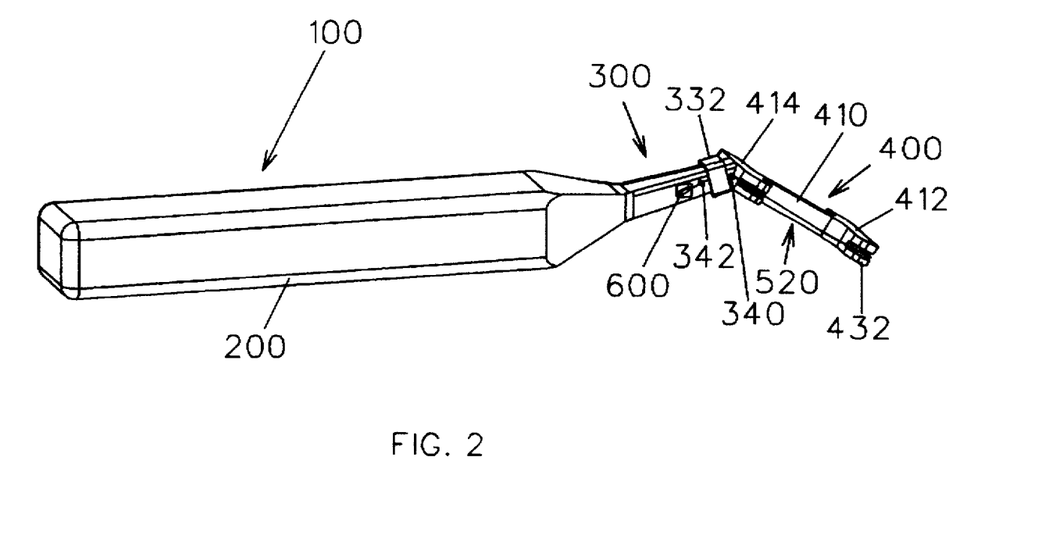
FIG. 2 is a perspective view of the flossing tool of FIG. 1 from the opposed side thereof.

On the opposed side of the neck 300 are first 340 and second spaced-apart tension pins 342 positioned on each side of the ridges 310. A cutting blade 600 extends from neck 300 and presents a sharp edge adjacent the tension pin 342.

Figure 1:
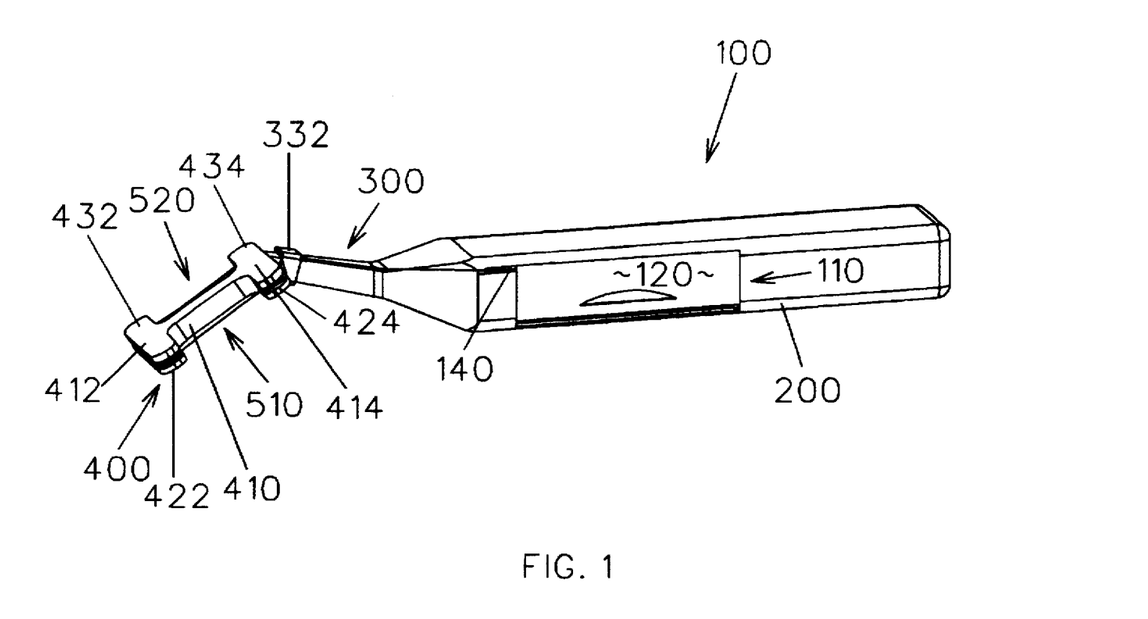
FIG. 1 is a perspective view of the flossing tool from one side thereof.
Figure 3:
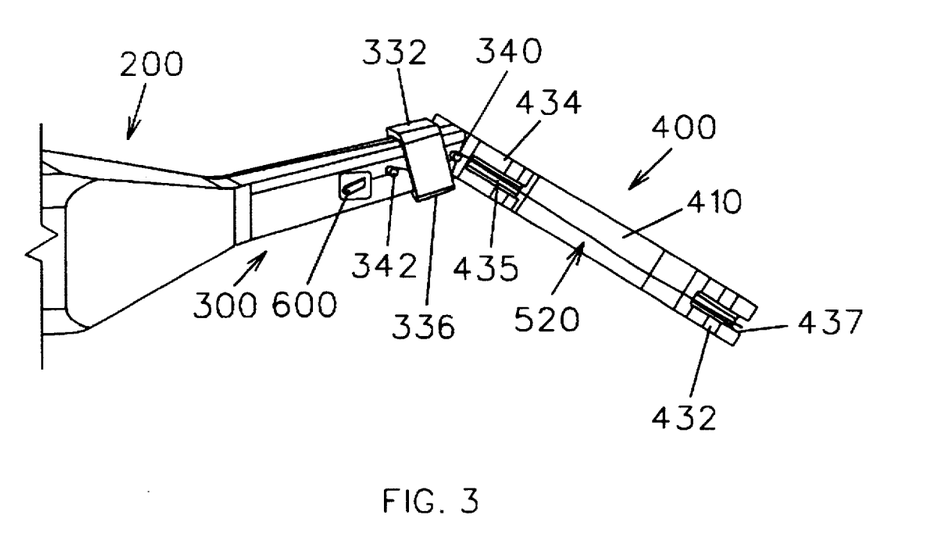
FIG. 3 is a fragmentary view of one end of the flossing tool of FIG. 2 on an enlarged scale.

In use the floss 500 is initially extended from compartment 110, along slot 140 and the top on the neck 300 and across the ridges 310. The floss is then guided through the respective channels 425, 423, 433, 435 in each of the lobes 424, 422, 432, 434 and wound about the tension pins 340, 342 so as to present an initial tension to the wound floss 500. Subsequently, clamp 332 of the locking device 330 is swung from its open FIG. 1 position to its locked position about neck 300 as shown in FIG. 3. A lip 336 on clamp 332 engages the underside of neck 300 so as to maintain the clamp 320 in its locked position. As such, the floss is trapped between the meshed ridges 310, 334 so as to place an additional tension on the wound floss 500.

As such, first and second spaced-apart stretches 510, 520 of floss 500 are positioned on opposed sides of the head 400 for user flossing of the upper and/or lower toothlines without the need to excessively manipulate the tool 100. The tension pins 340, 342 and locking device 330 places and maintains these floss lines 510, 520 under sufficient functional tension so that such lines 510, 520 will not collapse during user flossing. Accordingly, the user can insert the floss head 400 into his/her mouth and floss the appropriate teeth with no need to place the fingers within the oral cavity.

Upon completion the locking device 330 is moved to its open position with the free end of the floss unwrapped from the tension pins 340, 342. The previously used portion of the floss may then be severed by the cutter blade 600. A new portion of the floss 500 can then be extended from the compartment 110 and positioned as above-described for subsequent use.

The tool 100, as above described, thus presents first and second properly tensioned floss lines 510, 520 which enables the user to floss the upper or lower teethlines without excessive manipulation of the tool. The floss head 400 being sized to easily fit into the mouth is also angled relative to the neck and handle, as above described, so as to further aid the user in effective flossing.

It is to be understood that while a certain form of this invention has been illustrated and described, it is not limited thereto except insofar as such limitations are included in the following claims and allowable functional equivalents thereof.

Having thus described the invention, what is claimed as new and desired to be secured by Letters Patent is as follows:

1. A dental floss tool comprising:
   an elongated handle having a first end and a second end;
   a compartment in said handle between said first end and said second end for holding a supply of dental floss;
   a slot formed in said handle adjacent said compartment which provides a path for dental floss to extend from said compartment;
   a neck having a first end and a second end, the neck first end being joined to the first end of said handle such that the neck extends from said handle;
   a plurality of ridges formed on and traversing said neck, wherein floss extending from said slot is adapted to pass across said ridges;
   a floss head attached to said second end of said neck, said head comprising:
      an elongated head body having a series of four spaceda-part lobes extending therefrom;
      a channel in each of said lobes for holding said floss such that there are first and second longitudinal stretches of floss wound about said lobes;
   a pin extending from said neck for wrapping of a free end of the dental floss about said pin in a manner to place an initial tension on the dental floss wound about said lobes;
   a clamping device pivotally attached to said neck between a first position displaced from said ridges and a second position for engaging said ridges and floss passing thereover, said clamping device adapted to place additional tension on said dental floss wound about said lobes when in said second position.

2. The tool as claimed in claim 1 wherein two of said four lobes are positioned on one side of said elongated head body and the other two of said four lobes are positioned on an opposed side of said elongated head body.

3. The tool as claimed in claim 1 wherein said neck is angled relative to said handle.

4. The tool as claimed in claim 3 wherein said elongated head body is angled relative to said neck.

5. The tool as claimed in claim 1 further comprising a blade on said neck for severing a portion of a free end of the floss.

6. The tool as claimed in claim 1 further comprising means on said clamping device for releasably locking said clamping device to said neck at said second position.

7. A dental floss tool comprising:
   an elongated handle having a first end and a second end;
   means on said handle between said first end and said second end for holding a supply of dental floss;
   a neck having a first end and a second end, the neck first end being joined to the first end of said handle such that the neck extends from said handle;
   means on said neck for providing a path for the dental floss thereacross;
   a head attached to the second end of said neck, said head comprising:
      an elongated head body having a series of four spaced-apart lobes extending therefrom, said lobes defining corners of said head;
      means in each of said lobes for holding said floss such that there are first and second longitudinal stretches of floss wound about said lobes;
   a pin extending from said neck for wrapping of a free end of the dental floss about said pin and placing an initial tension on the dental floss wound about said lobes;
   a clamping device pivotally attached to said neck between a first position displaced from said neck and a second position for engaging said path providing means on said neck and the dental floss thereacross, said clamping device adapted to place additional tension on said dental floss wound about said lobes when in said second position.

8. The tool as claimed in claim 7 wherein two of said four lobes are positioned on one side of said elongated head body and the other two of said four lobes are positioned on an opposed side of said elongated head body.

9. the tool as claimed in claim 7 wherein said neck is angled relative to said handle.

10. The tool as claimed in claim 7 wherein said elongated head body is angled relative to said neck.

11. The tool as claimed in claim 7 further comprising a blade on said neck for severing a portion of a free end of the floss.

12. The tool as claimed in claim 6 further comprising means on said clamping device for releasably locking said clamping device to said neck at said second position.

13. A dental floss tool comprising:
   a handle having a first end and a second end;
   means between said handle ends for holding a supply of dental floss;
   a neck having first and second ends, said first end of said neck extending from said handle first end;
   a first clamping means on said neck for presenting a path for the dental floss, wherein floss extending from said holding means is adapted to pass across said first clamping means;
   a floss head attached to said second end of said neck, said head comprising:
      a head body;
      a plurality of spaced-apart flanges extending from said body;
      means in each of said flanges for holding the dental floss in extension about said head body in a manner to present first and second longitudinal stretches of dental floss supported by said head body;
   means extending from said neck for anchoring a free end of the dental floss thereto and placing an initial tension on the stretches of the dental floss;
   a clamping device supporting a second clamping means adapted for engaging said first clamping means, said device movably attached to said neck between a first position displaced from said neck and a second position for engaging said first and second clamping means with the dental floss extending therebetween, said engaged clamping means adapted to place additional tension on said dental floss stretches wound about said head body.

14. The tool as claimed in claim 13 wherein said holding means comprises a compartment in said handle.

15. The tool as claimed in claim 13 wherein said anchoring means comprises a pin extending from said neck for wrapping a free end of the dental floss therearound.

16. The tool as claimed in claim 13 further comprising means on said clamping device for locking said clamping device to said neck whereby to maintain said first and second clamping means in said engagement.

17. A dental floss tool comprising:

a handle having a first end and a second free end;

means between said handle ends for holding a supply of dental floss;

a neck having first and second ends, said first end of said neck extending from said handle first end;

an array of first meshwork-like elements on said neck, wherein a portion of floss extending from said holding means is adapted to pass across said first meshwork elements;

a floss head attached to said second end of said neck, said head comprising:
  a head body;
  a plurality of spaced-apart flanges extending from said body;
  means in each of said flanges for holding the dental floss in extension about said head body in a manner to present at least one longitudinal stretch of dental floss supported by said head body;

means extending from said neck for anchoring a free end of the dental floss thereto and placing an initial tension on said at least one stretch of the dental floss;

an array of second meshwork-like elements adapted for engagement with said first meshwork elements;

means for swingably attaching said array of second meshwork elements to said neck between a first position displaced from said first meshwork elements on said neck and a second position wherein said first and second meshwork elements mesh one with the other with said dental floss portion therebetween, said meshed first and second meshwork elements adapted to place additional tension on said at least one dental floss stretch supported by said head body.

18. The tool as claimed in claim 17 wherein said plurality of flanges are positioned about said head body to present first and second longitudinal stretches on opposed sides of said head body and supported thereby.

19. The tool as claimed in claim 17 further comprising means on said attaching means for releasably locking said attaching means at said second position.

* * * * *